United States Patent
Vaidya

(10) Patent No.: US 8,398,635 B2
(45) Date of Patent: *Mar. 19, 2013

(54) METHOD AND APPARATUS FOR MINIMALLY INVASIVE TREATMENT OF UNSTABLE PELVIC RING INJURIES

(76) Inventor: Rahul Vaidya, Tecumseh (CA)

(*) Notice: Subject to any disclaimer, the term of this patent is extended or adjusted under 35 U.S.C. 154(b) by 511 days.

This patent is subject to a terminal disclaimer.

(21) Appl. No.: 12/590,988

(22) Filed: Nov. 18, 2009

(65) Prior Publication Data

US 2010/0198267 A1  Aug. 5, 2010

Related U.S. Application Data

(63) Continuation-in-part of application No. 12/287,280, filed on Oct. 9, 2008.

(51) Int. Cl.
*A61B 17/56* (2006.01)
*A61B 17/58* (2006.01)
*A61F 2/30* (2006.01)

(52) U.S. Cl. .................. 606/60; 606/86 R; 606/286
(58) Field of Classification Search .............. 606/60–75, 606/246–331, 54, 57, 59
See application file for complete search history.

(56) References Cited

U.S. PATENT DOCUMENTS

| 5,234,431 A * | 8/1993 | Keller ........................ 606/70 |
| 5,951,557 A * | 9/1999 | Luter ......................... 606/286 |
| 2008/0108989 A1 | 5/2008 | Parsell et al. |
| 2010/0042149 A1 * | 2/2010 | Chao et al. .................. 606/246 |

OTHER PUBLICATIONS

Gardner, Michael and Nork, Sean. "Stabilization of Unstable Pelvic Fractures with Supraacetabular Compression External Fixation." Journal of Orthopaedic Trauma 21.4 (2007): 269-273.*
Sciulli, Robert. "CT-Guided Iliosacral Screw Placement: Technique and Clinical Experience." American Journal of Roentgenology 188 (2007): W181-W192.*

* cited by examiner

*Primary Examiner* — Andrew Yang
*Assistant Examiner* — Olivia C Chang
(74) *Attorney, Agent, or Firm* — David W. Schumaker

(57) ABSTRACT

The instant invention is a novel method for construct for temporary or definitive pelvic stabilization. The method uses the already established principles of anterior external fixation combined with internal hardware placed in a minimally invasive fashion. Fixation means are affixed to the ilia in the supra-acetabular position and a rigid, subcutaneous anteriorly bowed elongated plate is connected between the fixation means.

19 Claims, 13 Drawing Sheets

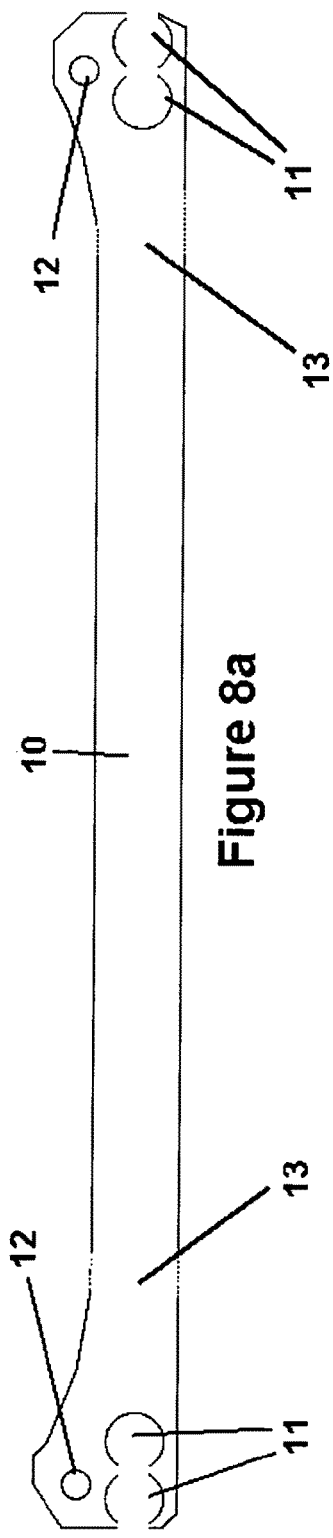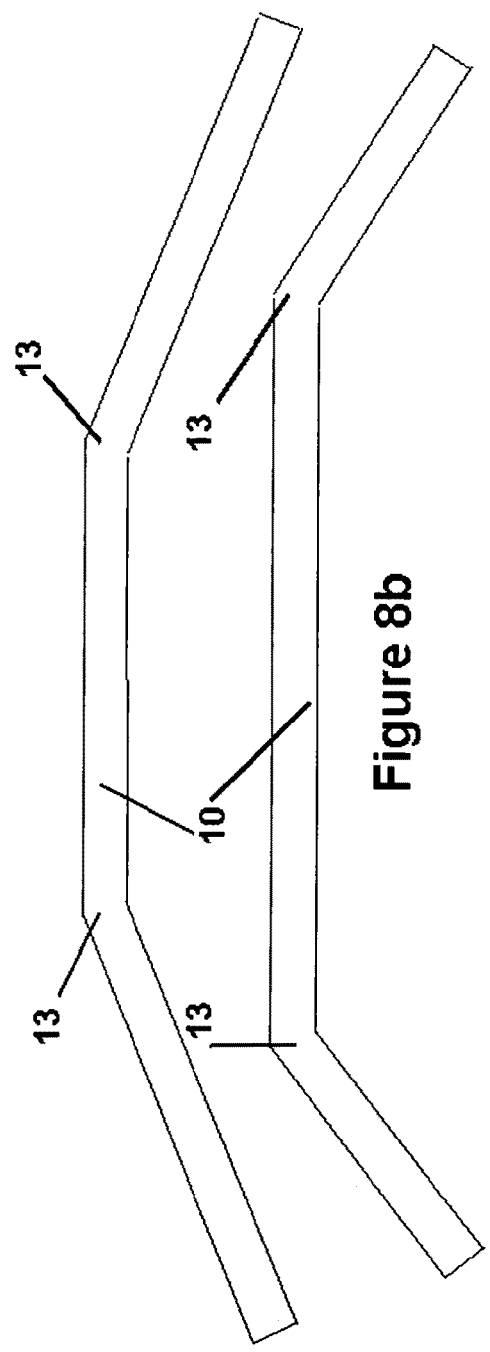

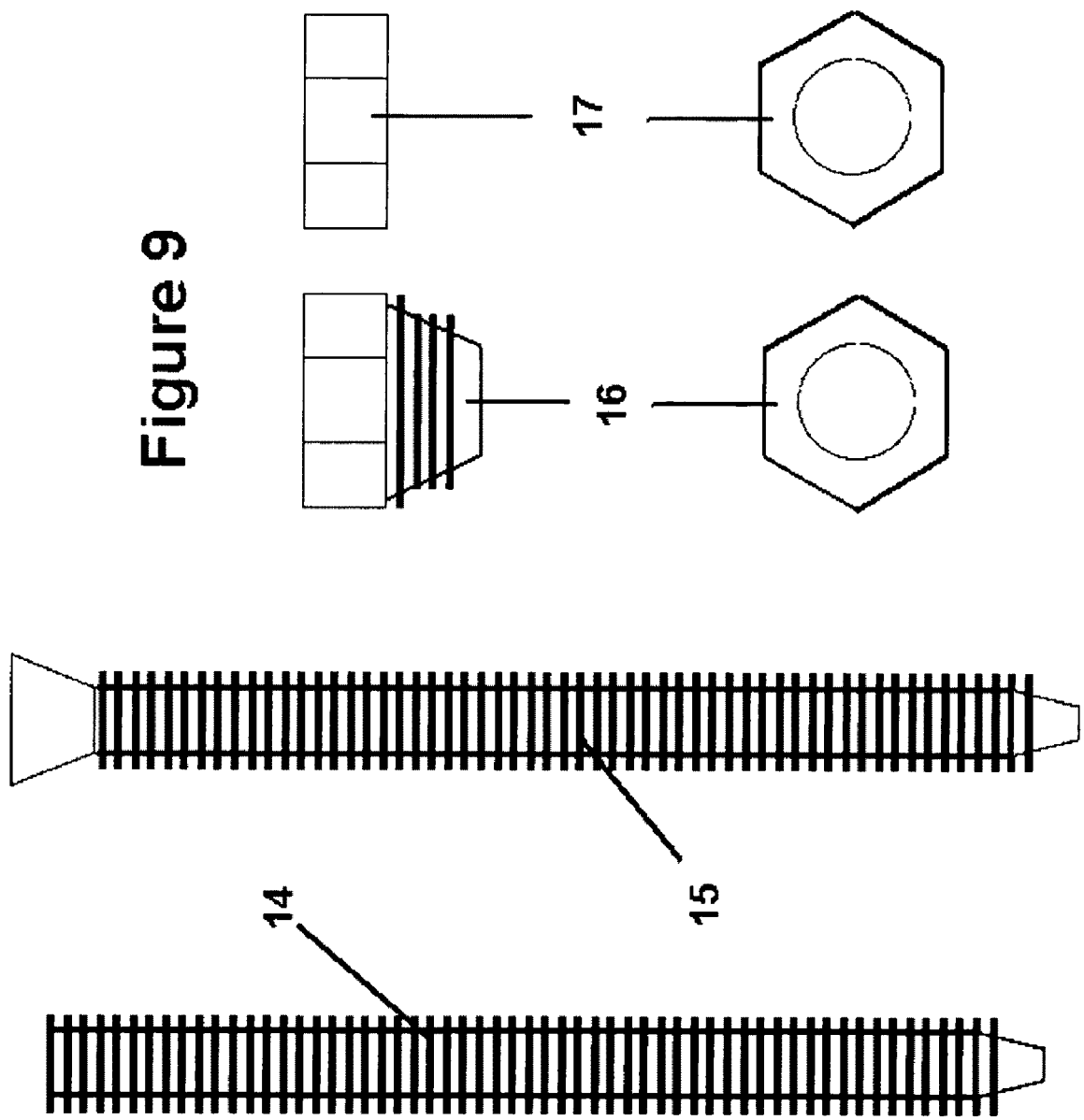

METHOD AND APPARATUS FOR MINIMALLY INVASIVE TREATMENT OF UNSTABLE PELVIC RING INJURIES

RELATED APPLICATIONS

The following application is a continuation in part of U.S. application Ser. No. 12/287,280 filed Oct. 9, 2008 and entitled "Method for Minimally Invasive Treatment of Unstable Pelvic Ring Injuries with an Internal Anterior Fixator and Posterior Iliosacral Screws."

FIELD OF THE INVENTION

The instant invention relates generally to methods and apparatus for the treatment of unstable pelvic fractures. More specifically the invention relates to a method and apparatus for minimally invasive treatment of unstable pelvic ring injuries using an internal anterior fixator and posterior iliosacral screws.

BACKGROUND OF THE INVENTION

Unstable pelvic fractures typically occur as a result of high-energy injuries such as automobile accidents, falls and the like. Even in this age of modern polytrauma care, acute pelvic fractures are potentially lethal. In the past, such injuries were treated without surgery. However, recovery to completely normal functionality was the exception rather than the norm. In more modern times, unstable pelvic fractures are treated surgically with a number of techniques depending on the type and extent of the fracture(s).

The pelvis consists of three major bones (two ilium and the sacrum) and some minor bones joined together in a ring shape and held by strong ligaments, See FIG. 1. General characteristics of pelvic fracture include severe pain, pelvic bone instability, and associated internal bleeding. Devices and methods used to treat fracture of the pelvis currently fall under two general classifications; internal fixation and external fixation. Combinations of both techniques are frequently chosen for certain fracture patterns.

Internal fixation is typically utilized when the patient exhibits unstable posterior pelvic fractures. Internal fixation refers to plates and screws applied directly onto the fracture sites after realignment. See, for example, U.S. Pat. Nos. 4,454,876; 5,108,397; 6,340,362 and 6,440,131. This type of fracture tends to be more complex with it involving multiple bony structures. Internal fixation addresses these clinical issues through open reduction and correction of misaligned bone segments that are subsequently stabilized with a wide variety of plate and screw methods.

Anterior pelvic fractures or hemodynamically unstable patients are candidates for external fixation. Pelvic external fixation consists of pins usually inserted into the iliac bones and then connected together by clamps and bars. See, for example, U.S. Pat. Nos. 4,292,964; 4,361,144; 5,350,378 and 6,162,222. External fixation methods consists of stabilizing the pelvic ring with a rigid framework residing outside the patient's body that is connected to the patient's pelvis via multiple pins that penetrate through the patient's soft and hard tissues. Several frame types are currently utilized. Two of the more widely deployed devices for external pelvic stabilization are the Hoffmann 2 Inverted "A" Frame and the Ganz Pelvic C Clamp.

The application of external reduction and fixation for pelvic fractures is advantageous compared to internal reduction and fixation due to its speed of deployment and lower level of technical training required for utilization. The primary disadvantages of external fixation of pelvic fractures include high risk of pin tract infections, and general patient discomfort. Also, the external frame physically blocks subsequent surgery on the abdomen and they are frequently difficult to fit to obese patients.

The instant inventor has developed a novel method using the already established principles of anterior external fixation. By combining these principles with internal hardware placed in a minimally invasive fashion, this technique allows for definitive pelvic stabilization without having the issues and co-morbidities of an external fixator (i.e. interfering with other procedures, pin care, patient acceptance, later conversion to internal fixation, etc.)

SUMMARY OF THE INVENTION

A surgical method for minimally invasive treatment of unstable pelvic ring injuries which includes the steps of affixing at least one fixation means to each of the first and second ilium of the pelvis, and attaching a rigid, anteriorly bowed subcutaneous elongated plate to at least one of said fixation means on each ilium. The fixation means may be affixed to the supra-acetabular area of each ilium of the pelvis. The fixation means may comprise threaded rod.

The step of affixing said threaded rod may comprise the steps of: creating a longitudinal incision centered between the Anterior Inferior Iliac Spine (AIIS) and the Anterior Superior Iliac Spine (ASIS); bluntly dissecting through the soft tissues; using fluoroscopic imaging to identify the supra-acetabular starting point for the pedicle screw; opening the cortex of the ilium at said starting point with a drill; establishing a corridor between the inner and outer cortices of the ilium using a pedicle finder; and screwing said threaded rod into said corridor.

The step of screwing said threaded rod into said corridor may comprise screwing the threaded rods such that the threaded rod in the second ilium is not initially fully inserted into the second ilium. The surgical method may comprise the further step of subcutaneously tunneling the elongated plate from one of the fixation means on one ilium to another of the fixation means on the other ilium before the step of attaching the elongated plate. The elongated plate may have at least one hole/slot in each end to accommodate the fixation means which affix the plate to the ilia of the pelvis.

The attaching step may further include the steps of: threading a first threaded nut onto the threaded rod affixed to the first ilium; inserting the threaded rod affixed to the first ilium into the hole/slot in one end of the elongated plate, the elongated plate resting on the first threaded nut; threading a second threaded nut onto the threaded rod affixed to the first ilium; and tightening the second threaded nut against the elongated plate such that the first threaded nut and the second threaded nut hold the elongated plate securely to the threaded rod affixed to the first ilium.

The elongated plate may further include a further hole in each end thereof and the method may further include the step of inserting a stabilization screw through the further hole on the end of the elongated plate adjacent to the first ilium and into the first ilium. The hole/slot in the end of the elongated plate adjacent to the second ilium may not be enclosed by the outer edge of the elongated plate.

The attaching step may further include the steps of: threading a first threaded nut onto the threaded rod affixed to the second ilium; inserting the threaded rod affixed to the second ilium into the hole/slot in the end of the elongated plate adjacent the second ilium by slipping the rod through the non-enclosed end of the hole/slot, the elongated plate resting on the first threaded nut; threading a second threaded nut onto the threaded rod affixed to the second ilium; and tightening the second threaded nut against the elongated plate such that the second ilium is pulled into the proper position for fixation; and fully tightening the second threaded nut against the elongated plate such that the first threaded nut and the second threaded nut hold the elongated plate securely to the threaded rod affixed to the second ilium.

The method may further include the step of inserting a stabilization screw through the further hole on the end of the elongated plate adjacent to the second ilium and into the second ilium. The method may further include the step of inserting the threaded rod which is affixed to the second ilium the rest of the way into the second ilium. The elongated plate may have bends to give the plate an approximation of an arc shape. The elongated plate may be positioned with the arc anterior to avoid any potential compressive complications to genitourinary or neurovascular structures prior to the step of attaching.

The method may comprise the further step of leaving the fixation means and the elongated plate attached to the pelvis for 8 to 12 weeks and thereafter removing the fixation means and the elongated plate. The method may comprise the further step of stabilizing the posterior instability prior to the step of affixing the fixation means. The step of stabilizing the posterior instability may comprise inserting at least one iliosacral screw through the rear of one or both of the first and second ilium and into the sacrum.

BRIEF DESCRIPTION OF THE DRAWINGS

FIGS. 8a and 8b show different views of an elongated plate which may be used in an alternative embodiment of the present invention and is used in place of the bowed rod;

FIG. 9 depicts threaded rods, screws, caps, and nuts useful in conjunction with the alternative embodiment to affix the elongated plate to the pelvis.

DETAILED DESCRIPTION OF THE INVENTION

The instant invention is a novel method and construct for temporary or definitive pelvic stabilization. The method uses the already established principles of anterior external fixation combined with internal hardware placed in a minimally invasive fashion. Stabilization of pelvic ring injuries is most often indicated when the volume of the pelvis is increased and/or an unstable pattern of injury is present. This stabilization method must be applied in the operating room under sterile conditions with adequate fluoroscopic guidance. It can be utilized in an emergent setting following provisional stabilization in the emergency room with a pelvic binder, sheet or clamp.

To aid in the determination of utilizing this anterior fixation method, we prefer the Tile classification since it is based on the concept of pelvic stability. In the Tile classification, type A fractures involve a stable pelvic ring. The partially stable type B lesions, such as "open-book" and "bucket-handle" fractures, are caused by external and internal rotation forces, respectively. In type C injuries, there is complete disruption of the posterior sacroiliac complex. These unstable fractures are almost always caused by high-energy severe trauma associated with motor vehicle accidents, falls from a height, or crushing injuries. Type A and type B fractures make up 70% to 80% of all pelvic injuries. This fixation method is typically considered for Tile B and C type injuries. In many patients with partially stable injury patterns, the presence of significant pain with upright posture can be alleviated with the addition of anterior fixation. Supra-acetabular fixation has been shown to have biomechanical advantages compared to iliac crest fixation. If adequate reduction cannot be obtained in a closed manner, then more traditional open reduction techniques need to be employed.

Surgical Technique

The patient may be positioned in the supine position on a radiolucent table. The skin may be prepped and draped from above the umbilicus to the proximal thigh. The lower extremity may be prepped into the field as well to facilitate reduction techniques.

Figure 1:
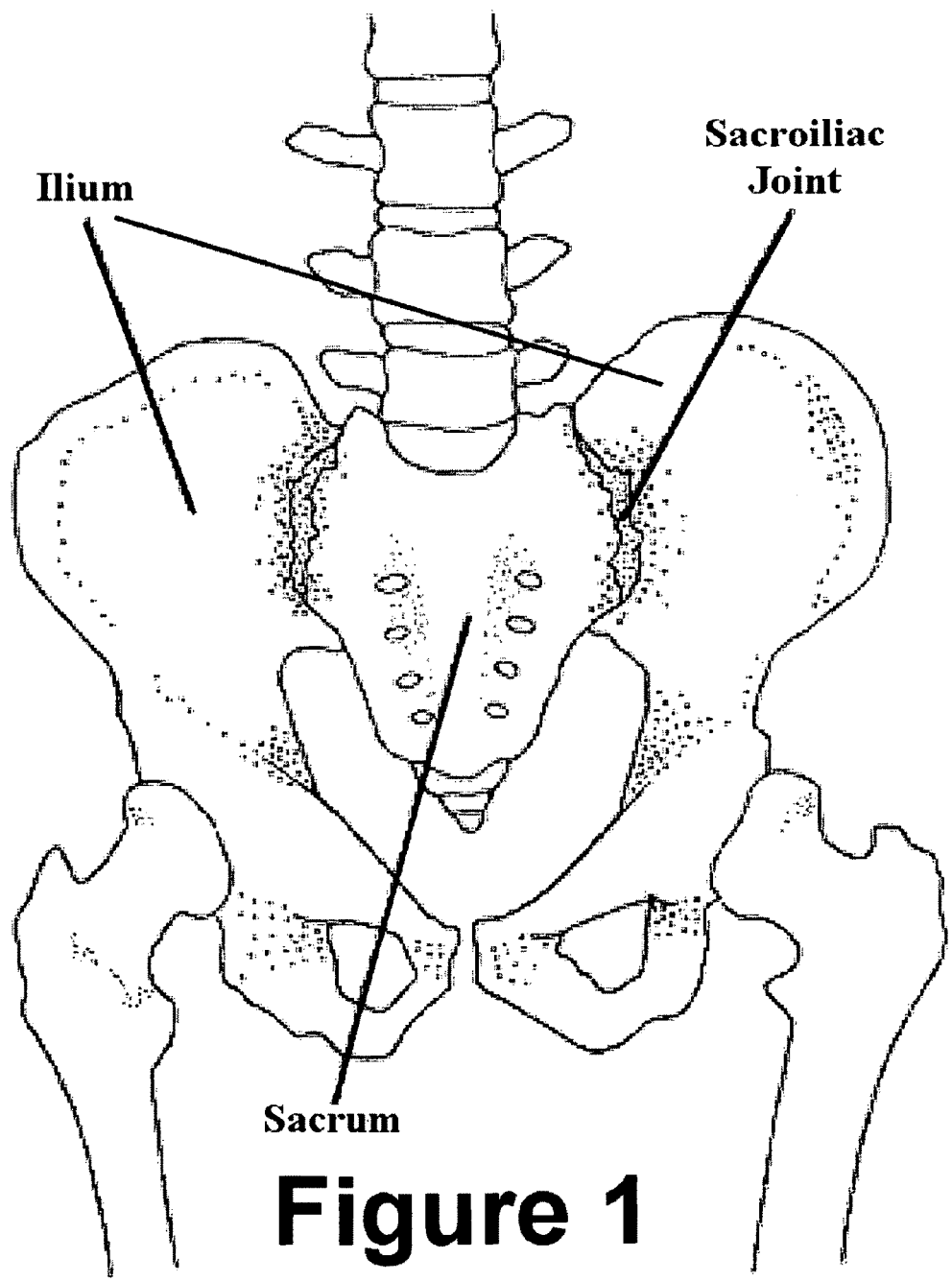
FIG. 1 shows a diagrammatic depiction of a pelvis.
Figure 2:
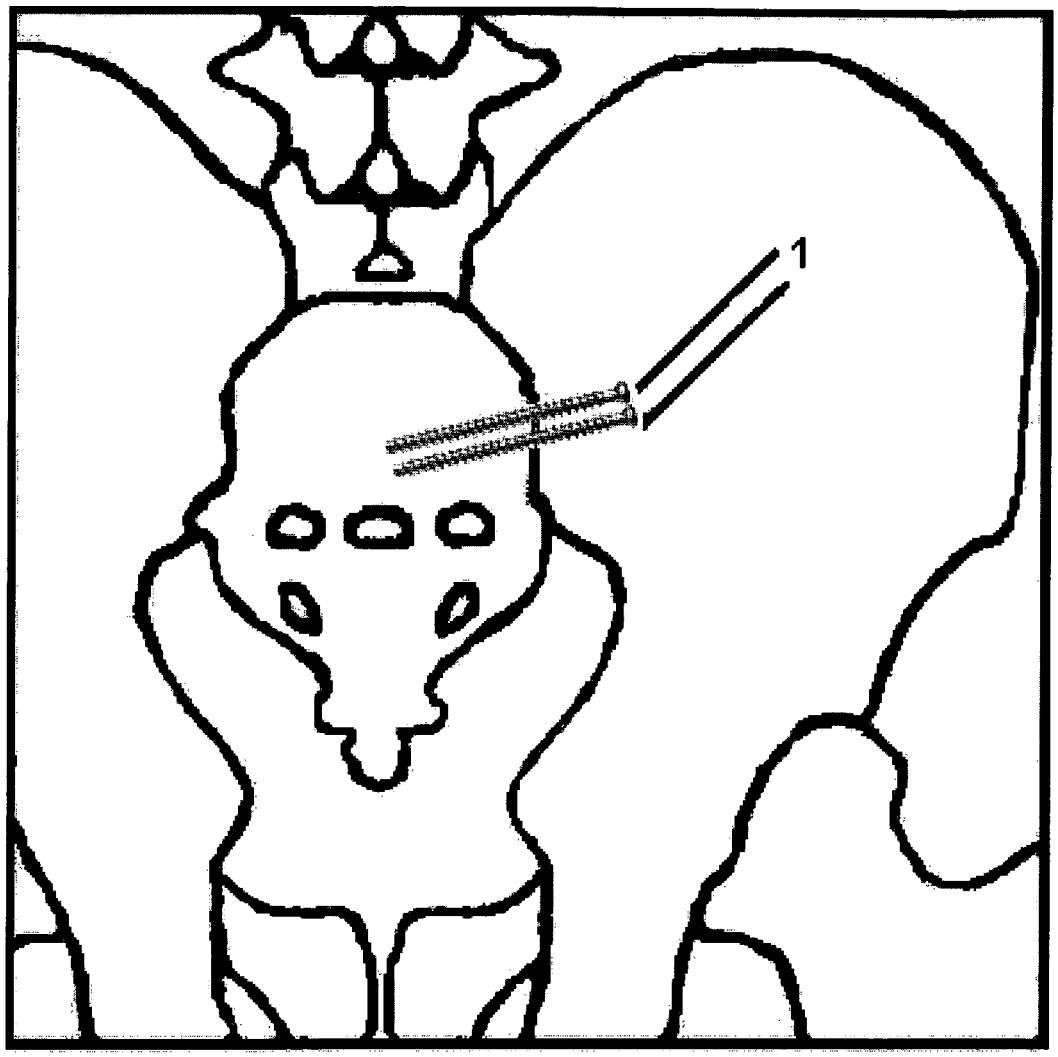
FIG. 2 shows the method in which iliosacral screws are used to perform posterior stabilization of the sacroiliac joint of the pelvis.
Figure 3:
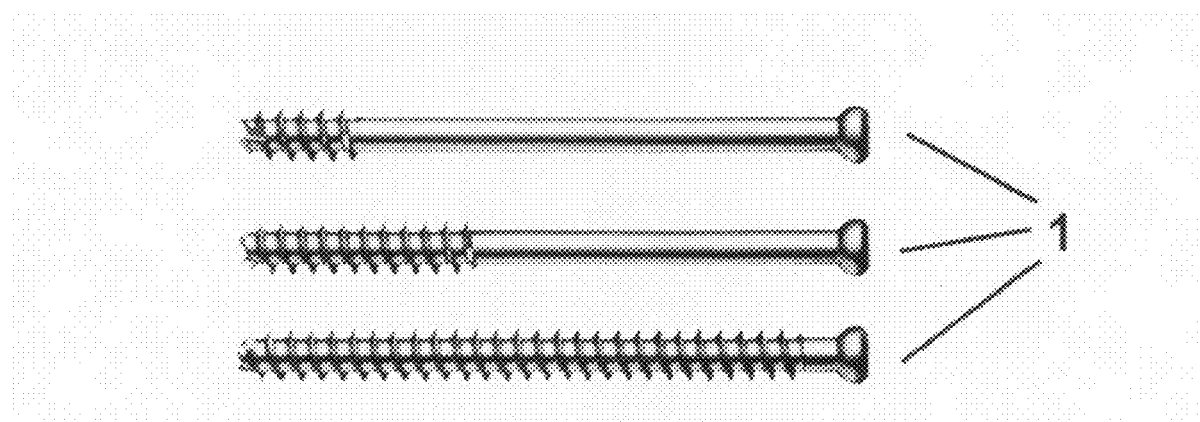
FIG. 3 depicts a variety of iliosacral screws useful for the posterior stabilization of the sacroiliac joint of the pelvis.

The posterior instability may be addressed first. The procedure for placement of iliosacral screws for posterior pelvic instability has been well described and will not be discussed here. See for example "CT-Guided Iliosacral Screw Placement: Technique and Clinical Experience" by Robert L. Sciulli, et al., American Journal of Roentgenology 2007; 188: W181-W192 (reproduced at http://www.ajronline.org/cgi/content/full/188/2/W181). FIG. 2 illustrates the way in which iliosacral screws 1 are inserted through the rear of the ilium and into the sacrum, thus stabilizing the posterior instability. FIG. 3 depicts typical iliosacral screws 1.

After stabilizing the posterior elements via the iliosacral screws, the anterior pelvis may be addressed. A longitudinal incision (preferably 2-3 cm in length) may be made centered between the Anterior Inferior Iliac Spine (AIIS) and the Anterior Superior Iliac Spine (ASIS). Blunt dissection may be used through the soft tissues. Potential dangers in this area include the lateral femoral cutaneous nerve, and care should be taken not to violate the hip capsule. Fluoroscopic imaging may be used to identify the starting point of the supra-acetabular fixation screw. The beam should be directed in an obturator oblique and pelvic outlet direction in order to isolate the appropriate column of bone for screw placement. A recent article by Gardner and Nork describes the appropriate placement of supra-acetabular pins in excellent detail. See "Stabilization of Unstable Pelvic Fractures With Supraacetabular Compression External Fixation", Gardner, et al., Journal of Orthopaedic Trauma 2007; 4:269-273. Once the appropriate starting point is identified, the cortex may be opened with a drill (preferably 5.0 mm). A pedicle finder is then used to establish a corridor between the inner and outer cortices of the ilium. Pedicle screws (preferably USS 8 mm×80 mm) are placed in the supra-acetabular position under fluoroscopic guidance.

Figure 4:
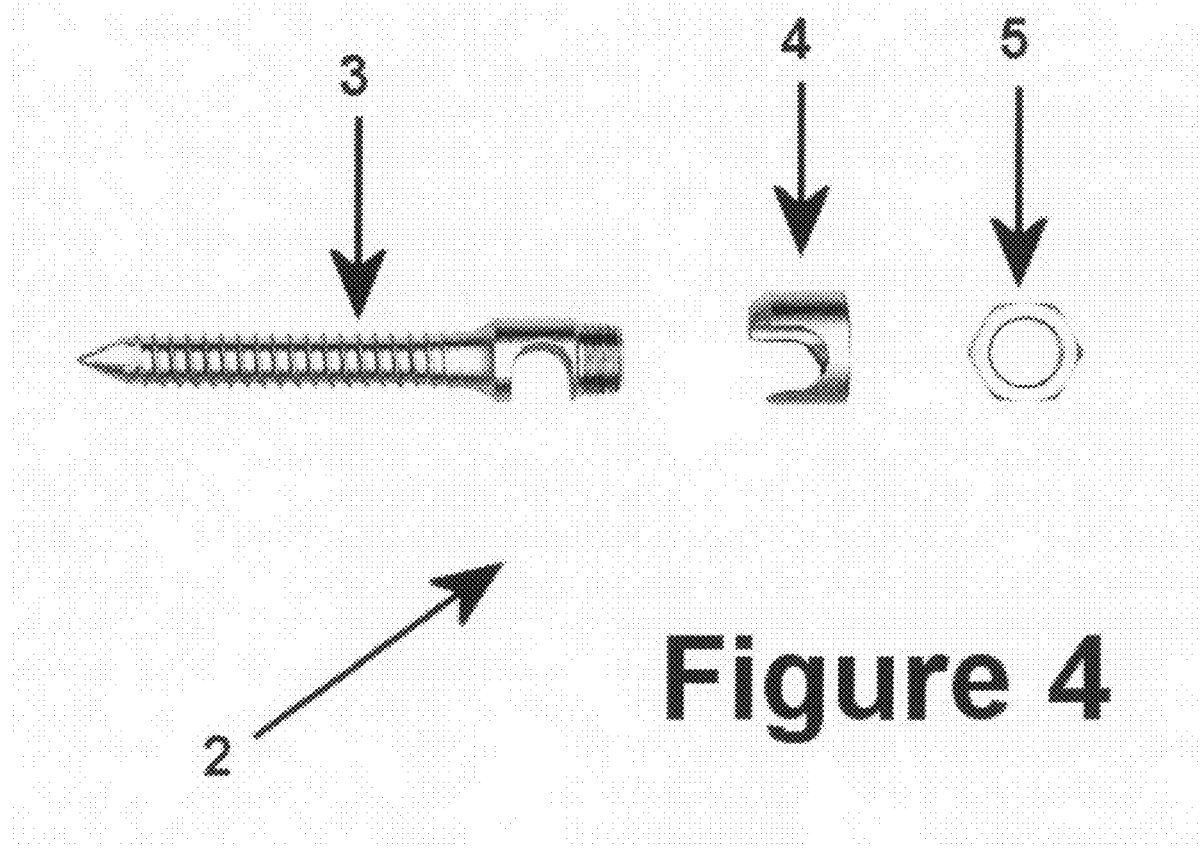
FIG. 4 depicts one embodiment of a pedicle screw system useful in the anterior pelvic stabilization surgical method of the present invention.
Figure 5:
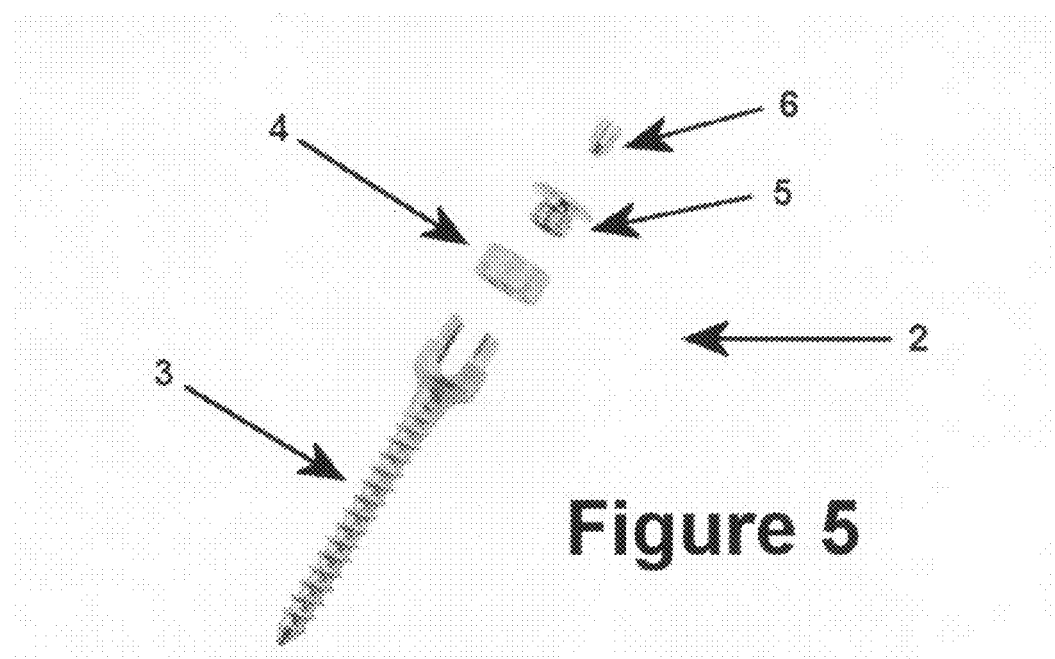
FIG. 5 depicts another embodiment of a pedicle screw system useful in the anterior pelvic stabilization surgical method of the present invention.
Figures 6A, 6B:
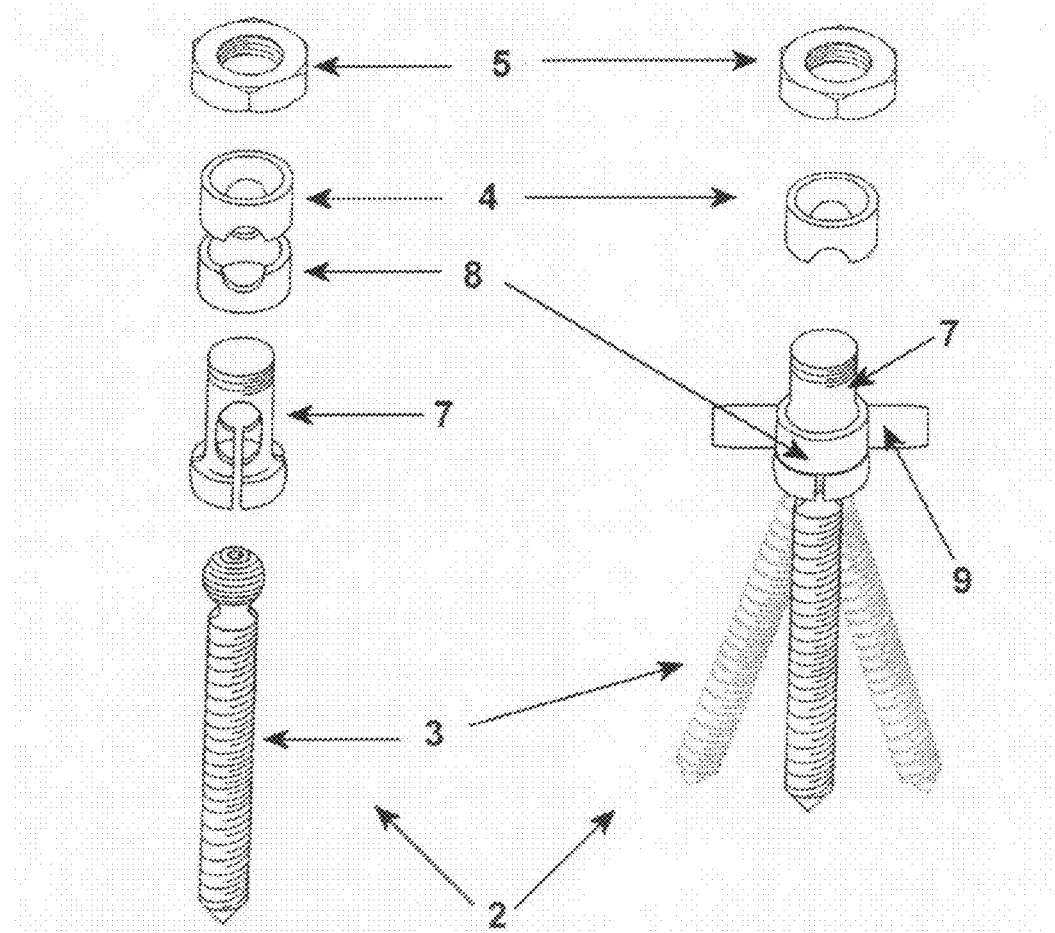
FIGS. 6a and 6b depict yet another embodiment of a pedicle screw system useful in the anterior pelvic stabilization surgical method of the present invention.

FIGS. 4, 5, 6a and 6b show exploded views of three different types of pedicle screw 2 which may be useful in the method of the present invention. Referring to FIG. 4, the separate parts of a side-opening pedicle screw can be seen. Specifically shown are the screw 3, the sleeve 4 and the nut 5. In use, the sleeve 4 and nut 5 are placed over the screw 3 and hold a rod in the cylindrical opening formed by the mating of the screw 3 and the sleeve 4. Turning to FIG. 5, a different type of pedicle screw 2 is seen. In this variety, there is still a screw 3, a sleeve 4 and a nut 5, but there is also a set screw 6 which helps to hold a rod in the opening between the screw 3 and the sleeve 4. Finally, FIGS. 6a and 6b show a polyaxial pedicle screw having a swivel joint. Once again this variety of pedicle screw has a screw 3, a sleeve 4 and a nut 5, but this type also has a mechanism consisting of a swivel clamp 7 and a swivel clamp collar 8. This added hardware allows the head of the pedicle screw to swivel somewhat independently from the screw 3. Thus this swivel head allows for ease of fit to curved rods 9 without the requirement for excessive rod contouring.

Returning to the surgical method, it should be noted that the screws are preferably not seated completely to the bone so that the connecting rod may be passed superficial to the sartorius muscles. A titanium rod 9 (preferably USS 6 mm) may then be pre-contoured with a bow, placed over the screws 2 and cut to the appropriate length on the back table. The rod may preferably be anywhere from 6 mm to 1 cm in diameter and may also be pre-bent for ease of use. The rod may then be tunneled subcutaneously from one screw to the other. Before connecting the rod, it may be positioned with the bow anterior to avoid any potential compressive complications to genitourinary or neurovascular structures. Also, any necessary reduction may be performed at this stage. Rotational and vertical alignment should be performed prior to attaching the rod, and preferably prior to tunneling the rod to limit pressure on the soft tissues. If posterior fixation is used, then most of the reduction should be complete at this point. This hardware system allows for compression and tensioning once the rod is in place. Reduction and hardware position may be assessed on fluoroscopic AP, inlet and outlet views. As an alternative to fluoroscopic AP, CT guidance may be used. The construct is intended as definitive treatment, with removal typically performed after 8 to 12 weeks. The timing of application and removal is ultimately determined on an individual case basis.

Figure 7:
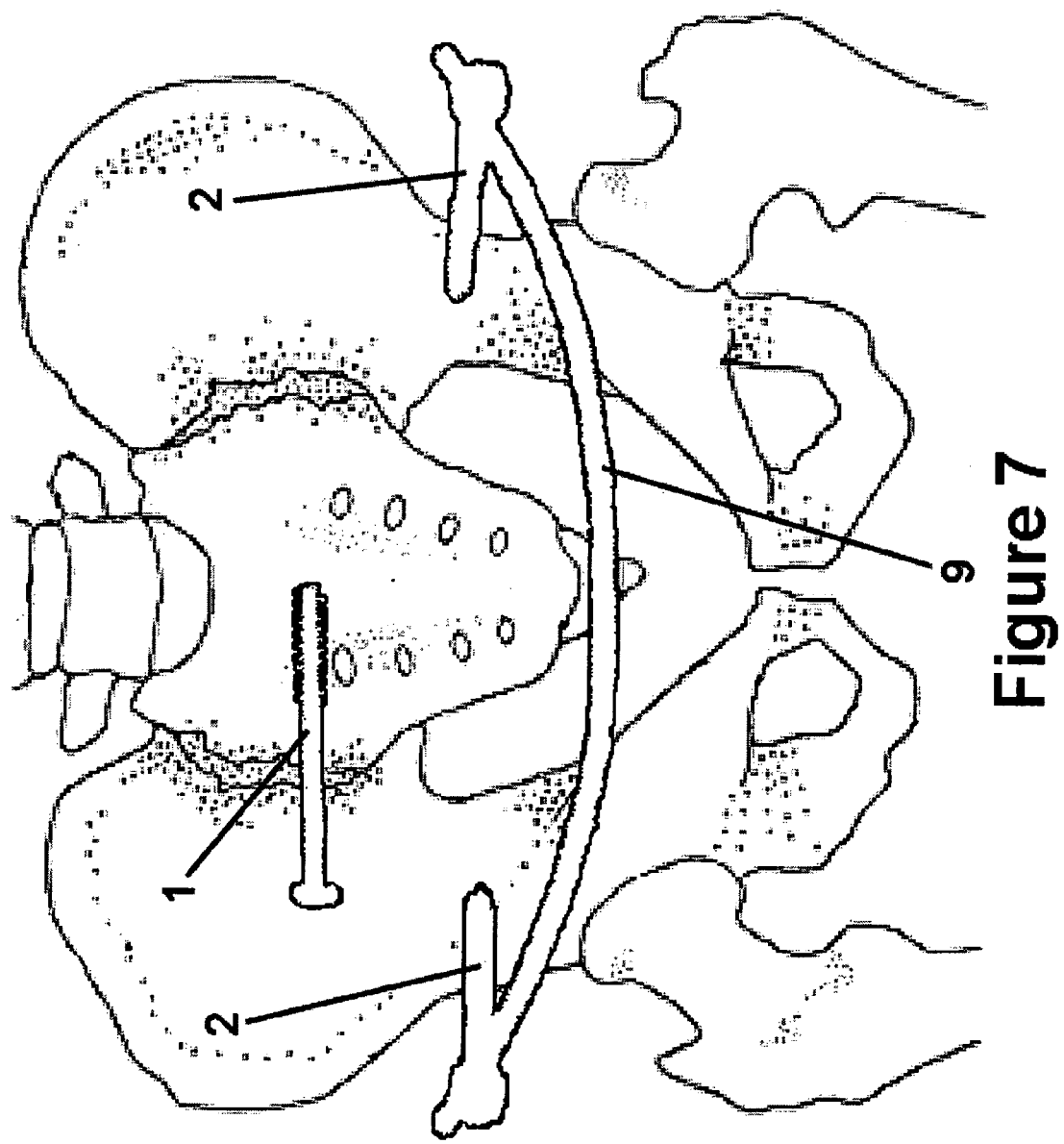
FIG. 7 is an x-ray of a patient who has had posterior stabilization of the sacroiliac joint of the pelvis using an iliosacral screw as well as the anterior stabilization surgical method of the present invention using two pedicle screws and an anteriorly bowed rod.

FIG. 7 shows an x-ray of a 32-year old male who was involved in a motor vehicle accident and upon whom the inventive surgical method was performed. As can be seen, the posterior was stabilized and fixated using an iliosacral screw 1. The anterior was fixated and stabilized by the inventive method using two pedicle screws 2, one attached to the supra-acetabular portion of each ilium. Connected between the pedicle screws 2 is a rigid, anteriorly bowed subcutaneous fixation rod 9.

The biomechanical stability of the inventive supra-acetabular pedicle screw internal fixation construct was evaluated and compared with the more prevalent external fixator. Three different pedicle screw constructs were compared to the external fixator, a mono axial screw system and two different polyaxial screw systems.

A total of 4 constructs were tested. These included: 1) an external fixation system; 2) a mono-axial pedicle screw system; 3) a polyaxial pedicle screw system (Click'X, a trademark of Synthes Inc., West Chester Pa.); and 4) another polyaxial pedicle screw system (Pangea, a trademark of Synthes Inc., West Chester Pa.). All constructs were assembled to have an active length of the longitudinal element equal to 280 mm. For the pedicle screws systems, screws were inserted into the test blocks, leaving an approximate 15 mm gap between screw head and test block. This resulted in a construct moment arm of 75 mm. The external fixator constructs were assembled with a 145 mm construct moment arm as this is where the fixator connection was measured to lie in a clinical setting.

Test Apparatus 1) an MTS RT/50 Electromechancial. Test Frame, from MTS Corp. (Eden Praire, Minn.), Calibrated: February 2008; and
2) an MTS Bionix Electromechanical Torsion Test Frame, from MTS Corp. (Eden Praire, Minn., Calibrated: March 2008.

Test Procedure

All constructs were tested first in axial compression. Loads were applied in the elastic range (20 mm displacement). Once axial testing was completed, 3 components were tested in torsion, within the elastic range (10°, and 2 were to failure. The three components tested within the elastic range (axial and torsion) were then retested in axial compression until failure.

Axial Testing:

Standard clevis fixtures were rigidly attached to the load cell and lower platen of the test machine. Constructs were mounted to the clevis fixtures using 12.7 mm diameter steel hinge pins.

An axial tensile load was applied to the construct at a test speed of 5 mm/min. Load-displacement curves were acquired for each construct tested and bending yield load, stiffness and ultimate bending failure load were calculated, as applicable. Yield load will calculation are based upon 0.020× the active length (5.6 mm). Note: testing was performed for a maximum of 75 mm of axial displacement. Results are shown in Table 1.

Torsion Testing:

Clevis fixtures that prevented rotation of the test block were rigidly attached to the load cell and lower plate of the test machine. Constructs were mounted to the clevis fixtures using 12.7 mm diameter steel hinge pins. Spacers, that prevent test block rotations about the hinge pins, were manually set.

An angular displacement was applied to the construct at a test speed of 60°/min. Axial load was maintained at 0 Newton. Torque-angular displacement curves were acquired for each construct tested and torsional yield load, stiffness and ultimate torque will be calculated, as applicable. Yield torque was based upon a 5° offset. Note: testing was performed for a maximum of 60° or angular rotation. Results are shown in Table 2.

TABLE 1

Summary Results - Axial

| Type | Peak Load (N) | Yield Load (N) | Bending Stiffness (N/mm) * | p-value (vs. Ex Fix) |
|---|---|---|---|---|
| External Fixator | 160 ± 4 | 102 ± 3 | 2.88 ± 0.05 | — |
| USS Monoaxial | 370 ± 15 | *** | 4.01 ± 0.11 | >0.0001 |
| Click'X Polyaxial | 158 ± 1 | *** | 3.64 ± 0.11 | >0.0001 |
| Pangea Polyaxial | 137 ± 1 | *** | 3.63 ± 0.15 | >0.0001 |

TABLE 2

| | Summary Results - Torsional | | | |
|---|---|---|---|---|
| Type | Peak Torque (N-mm) | Yield Torque (N-mm) | Torsional Stiffness (N-mm/°) * | p-value (vs. Ex Fix) |
| External Fixator | 14.70 | 4.92 | 0.50 ± 0.07 | — |
| USS Monoaxial | 5.94 | 4.47 | 0.38 ± 0.01 | 0.0163 |
| Click' X Polyaxial | 6.93 | 4.40 | 0.38 ± 0.04 | 0.0124 |
| Pangea Polyaxial | 6.99 | 5.26 | 0.38 ± 0.01 | 00055 |

The results show that the construct of pedicle screws is superior to the external fixator in axial loading. However, the torsional stiffness is greater with the external fixator.

While this embodiment has been described with respect to pedicle screws 2 that have been attached to the anterior of each ilium and the bowed fixation rod 9 has been bowed anteriorly away from the pelvis, the invention can alternatively call for the attachment of the pedicle screws 2 to the posterior of the ilia and the bowed fixation rod 9 can be bowed posteriorly away from the pelvis.

Alternative Embodiment

In an alternative embodiment, an anteriorly bowed subcutaneous elongated plate is used in place of the bowed rod. The elongated plate 10 is depicted in FIG. 8a. The plate 10 has at least one hole 11 in each end to accommodate the fixation means which affix the plate to the pelvis. Preferably the at least one hole 11 may be an elongated slot. More preferably the elongated slot is open on one end as shown in FIG. 8a. The elongated plate 10 may be bowed in a continuous arc or may have bends 13 (see FIG. 8b) to give the plate an approximation of an arc shape. The elongated plate 10 may be bent by the surgeon before insertion into the patient or may come pre-bent in a kit along with the fixation means. The pre-bent elongated plate 10 may come in a variety of lengths. It is believed that a most patients needs can be addressed using one size from a group of only three different sizes. The elongated plate 10 has a length much greater that its width and thickness. The elongated plate 10 may further include at least one additional hole 12 in each end through which stabilization fixation means may inserted into the pelvis.

Turning to FIG. 9, there is shown therein affixation devices useful for the present embodiment. Threaded rods 14 are used in conjunction with nuts 16 and 17 to hold the threaded rod 14 in the holes 11 at the ends of the elongated plate 10. Stabilization screws 15 are inserted through the additional holes 12 to further stabilize the elongated plate 10. The nuts 16 may be designed with a portion which fits into the hole/slot 11 assisting in fixing the threaded rod 14 to the elongated plate 10. The portion which fits into the hole/slot 11 may be threaded and may fit into threading in hole/slot 11. As with the previous embodiment, the elongated plate 10, threaded rods 14, stabilization screws 15, and nuts 16, 17 are all formed of a bio-compatible material such as, for example, titanium, stainless steel, or a bio-compatible and/or bio-adsorbable polymer.

FIGS. 10a to 10l depict the steps of a surgical method of using the elongated plate 10, threaded rods 14, stabilization screws 15, and nuts 16, 17 to fixate an unstable pelvic ring injury. The initial preparation is the same as that described above for the previous embodiment.

Figure 10A:
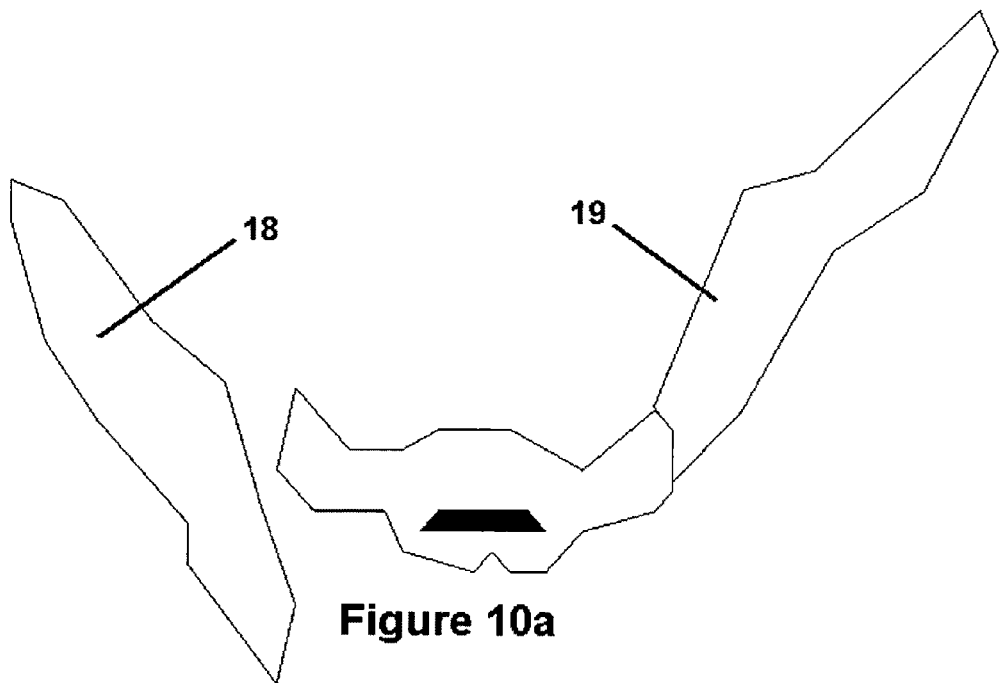
FIGS. 10a to 10l depict different stages in the surgical technique for fixation of the unstable pelvic ring injury using the elongated plate of FIGS. 8a and 8b using the threaded rods, screws, caps, and nuts of FIG. 9.
Figure 10B:
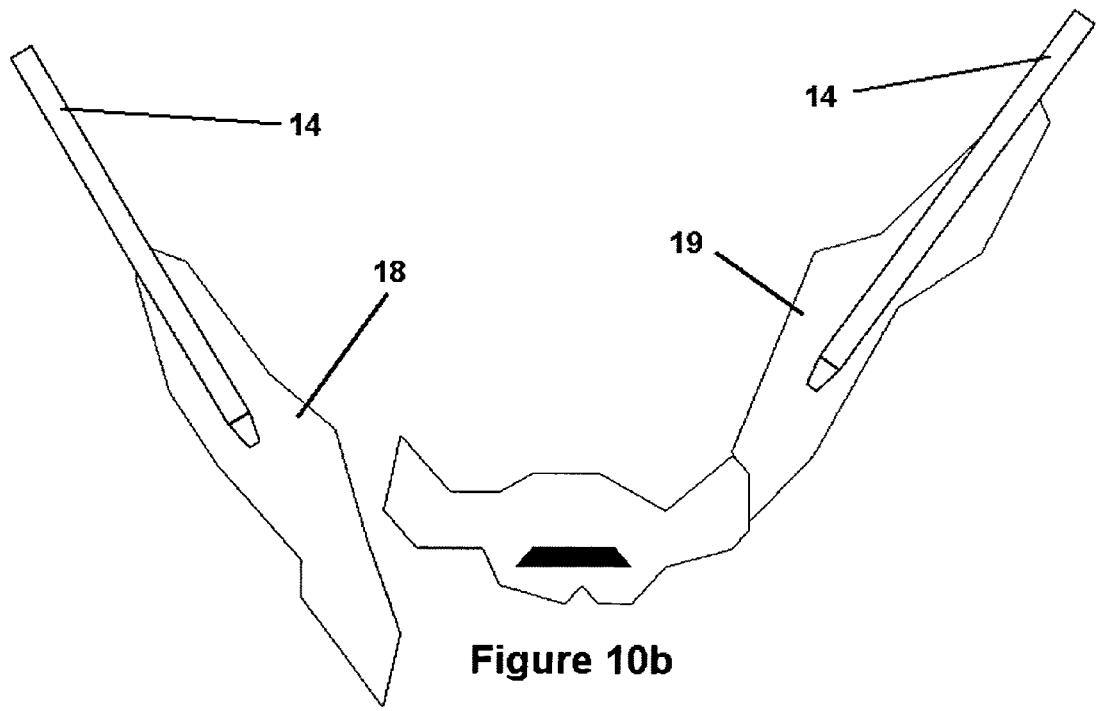

Referring now to FIG. 10a there is shown a schematic depiction of pelvis having an unstable pelvic ring injury. Specifically shown is an unstable ilium 18 and an intact ilium 19. It should be noted that the pelvic ring injury may result in both ilia being unstable and the inventive method for stabilization would be the same. Herein after the ilia will be known as the first and second ilium. Initially, threaded rods 14 are placed into both ilia 18, 19, as shown in FIG. 10b. Note that the threaded rod 14 which is affixed to the second ilium 18 is not fully inserted at this stage of the procedure.

Figure 10C:
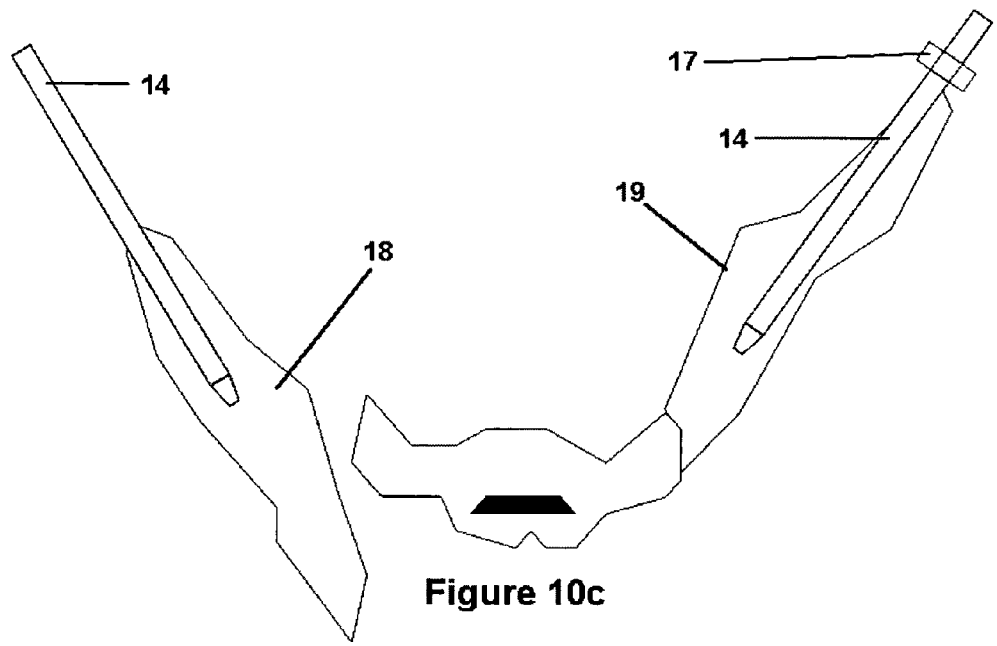
Figure 10D:
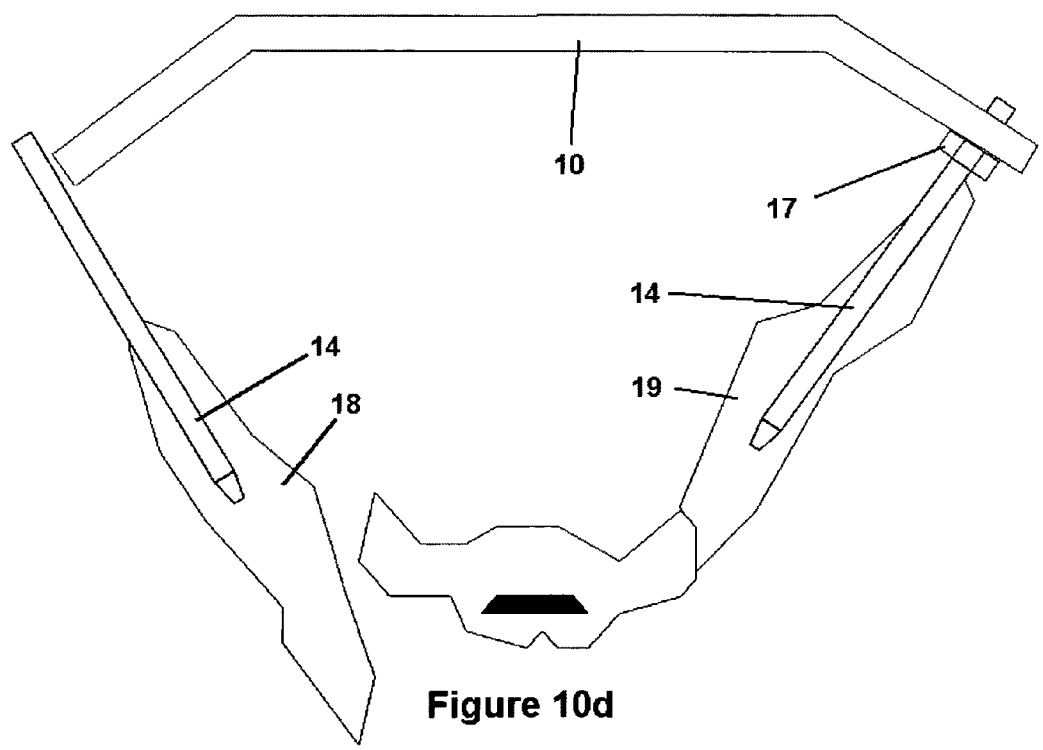

As in the previous embodiment, the threaded rods are placed into the supra-acetabular position using the technique described above. Once the threaded rods 14 are placed into both ilia 18, 19, a first threaded nut 17 is placed onto the threaded rod 14 which is affixed to the first ilium 19 as shown in FIG. 10c. One end of the elongated plate 10 is placed onto the threaded rod 14 which is affixed to the first ilium 19. The threaded rod 14 is inserted into the hole/slot 11 and the elongated plate rests adjacent the first threaded nut 17 as shown in FIG. 10d.

Figure 10E:
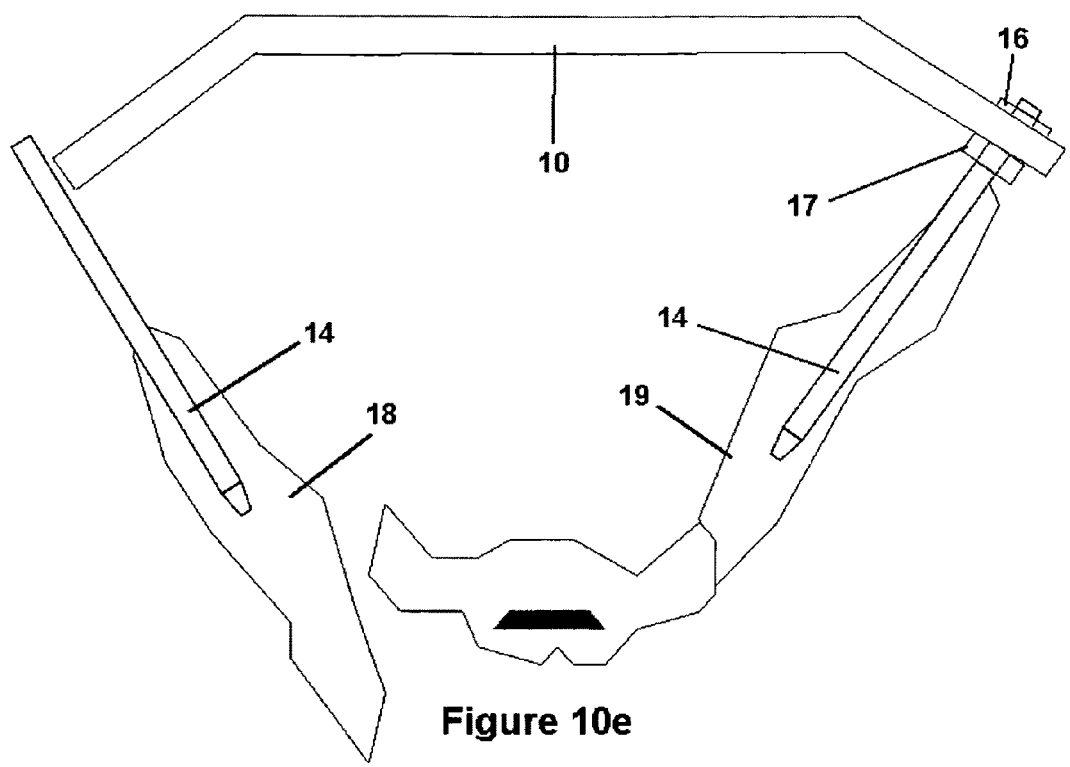
Figure 10F:
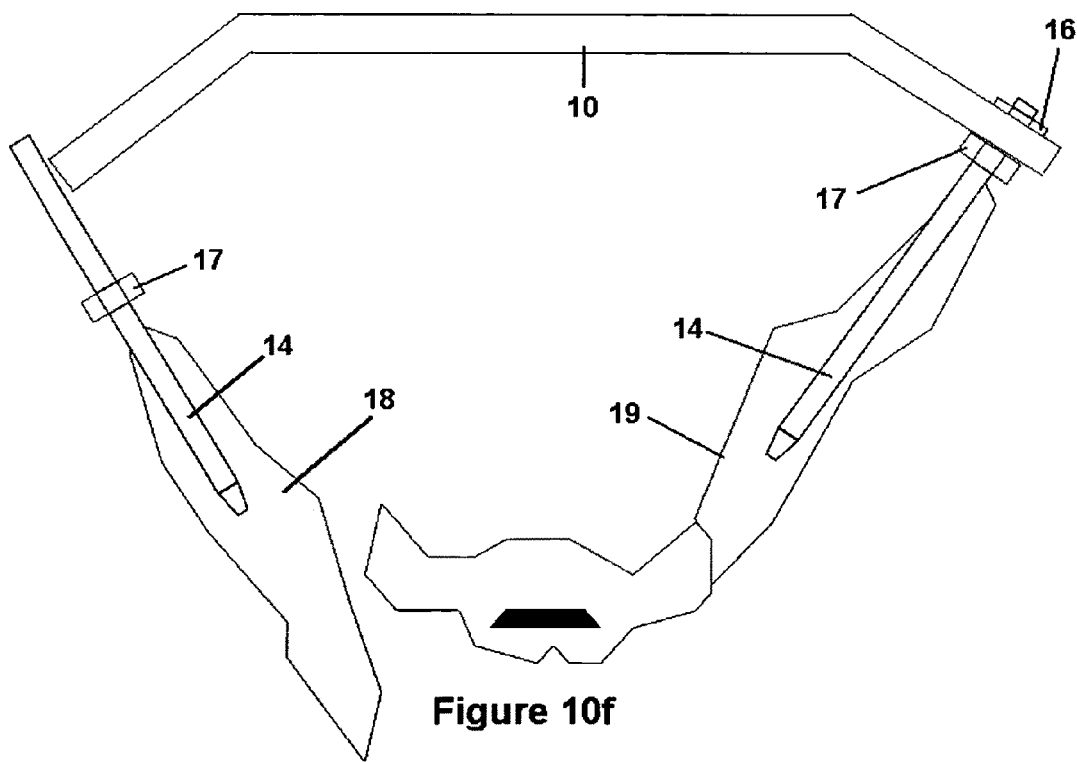
Figure 10G:
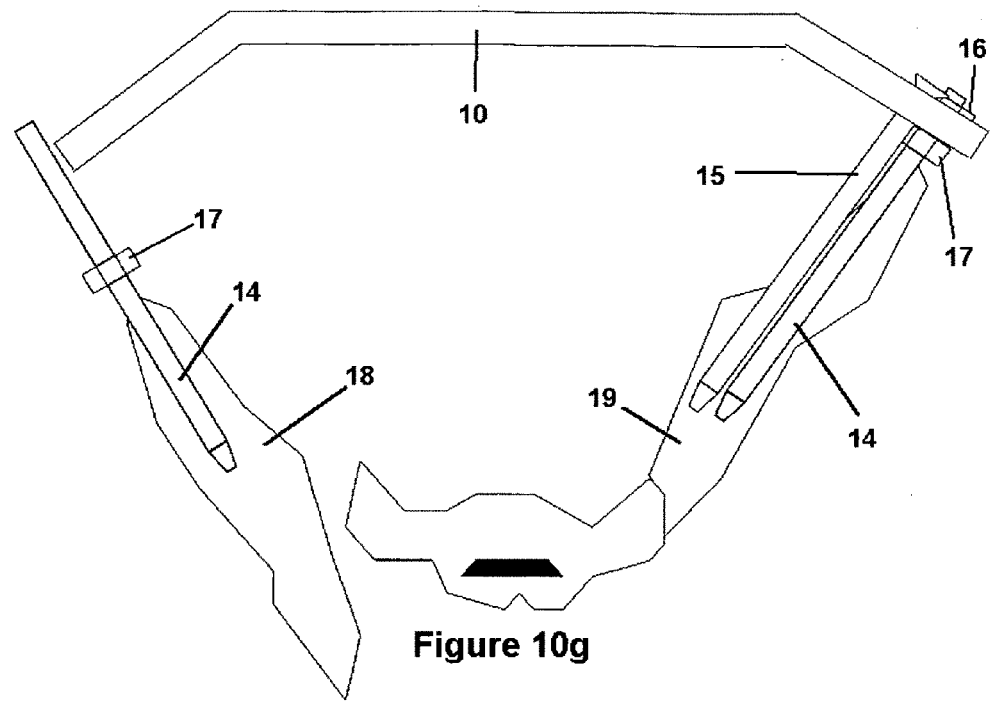

Once the plate is in place on the threaded rod 14 which is affixed to the first ilium 19, a second threaded nut 16 is attached to threaded rod 14 which is affixed to the first ilium 19 and is used in conjunction with first threaded nut 17 to fix the position of elongated plate 10 as shown in FIG. 10e. Next, a first threaded nut 17 is attached to the threaded rod 14 which is affixed to the second ilium 18 and a threaded stabilization screw 15 is inserted through additional hole 12 in the end of elongated plate 10 into the first ilium as shown in FIG. 10g.

Figure 10H:
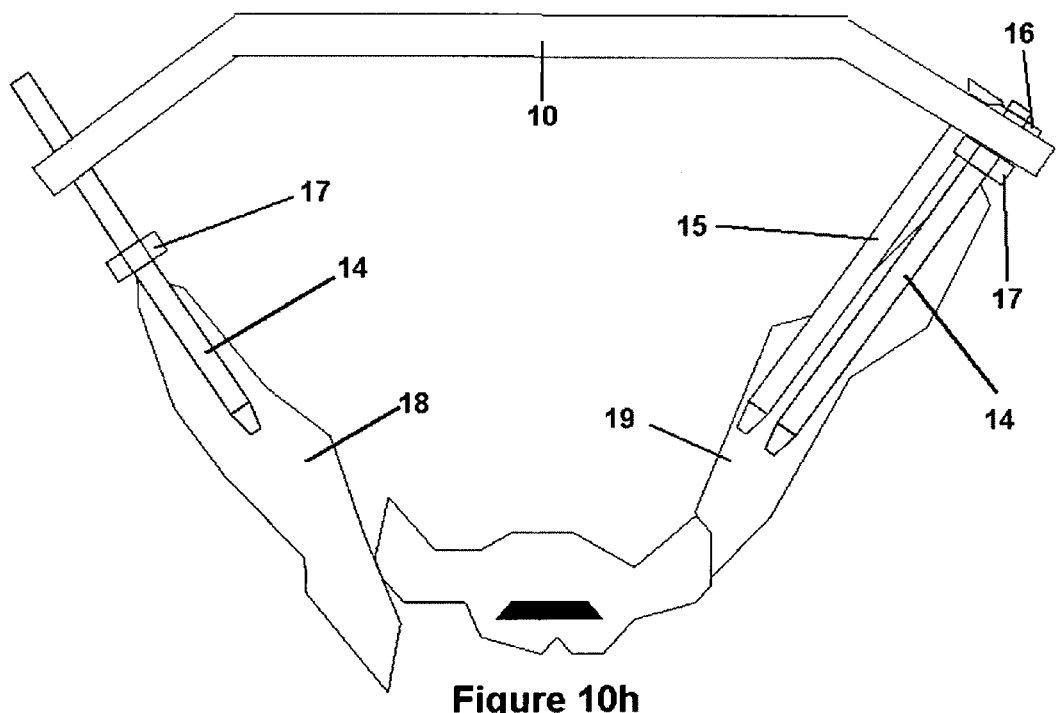
Figure 10I:
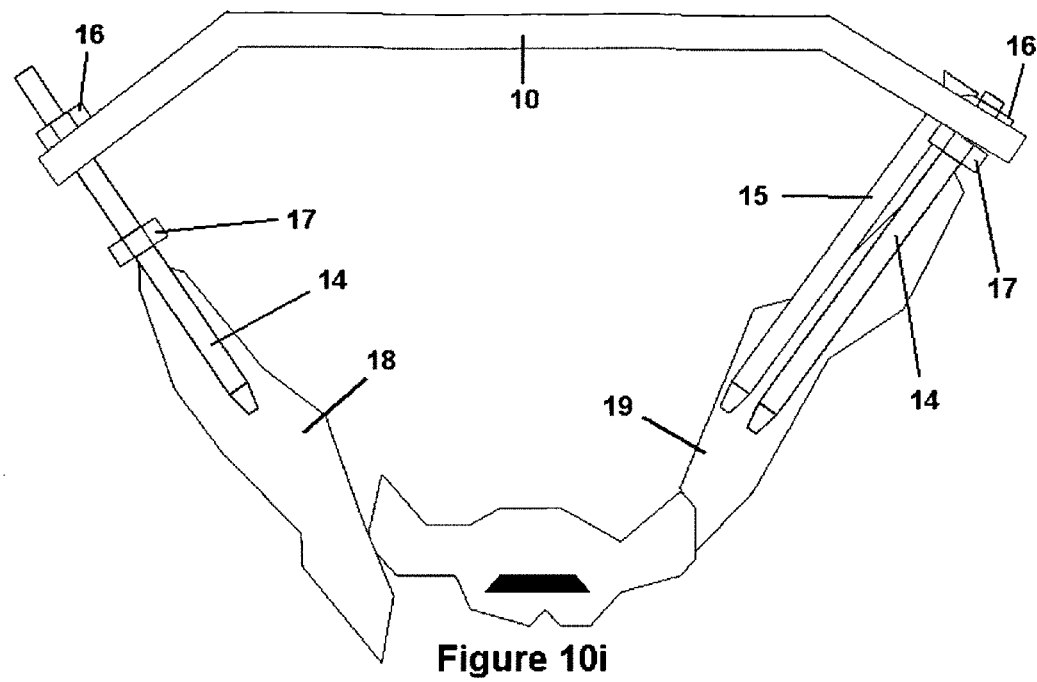
Figure 10J:
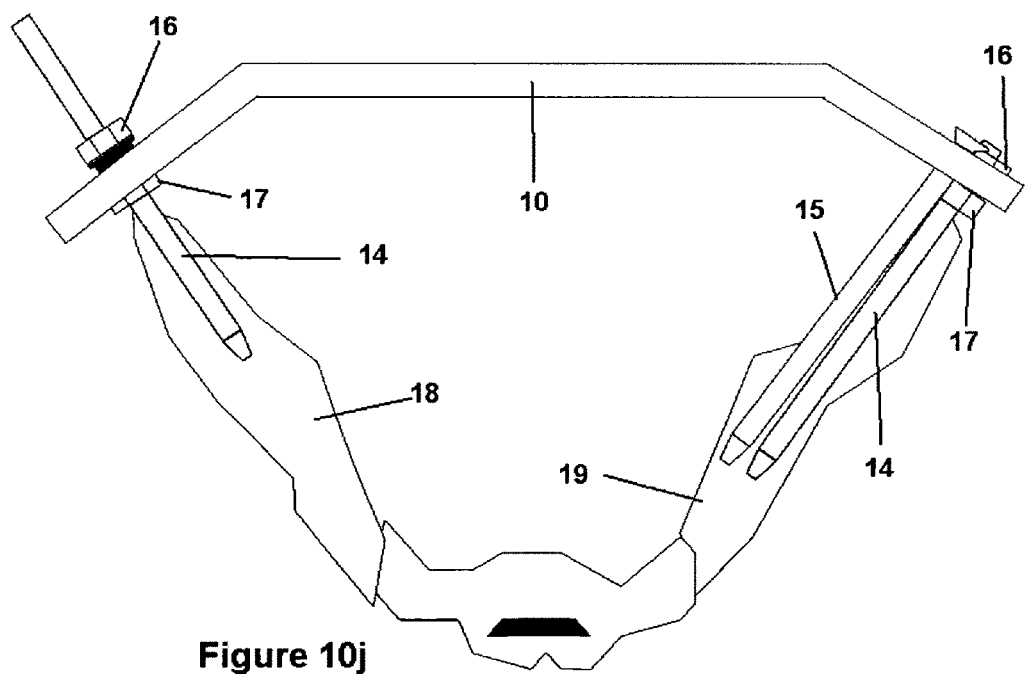

Next, the end of elongated plate 10 which is adjacent to the second ilium 18 is placed onto the threaded rod 14 which is affixed to the second ilium 18. This may be accomplished by slipping the threaded rod 14 into/through the open end of hole/slot 11 as shown in FIG. 10h. Next a second nut 16 is placed onto the threaded rod 14 which is affixed to the second ilium 18 a shown in FIG. 10i. Thereafter, second nut 16 which is threaded onto threaded rod 14 which is affixed to the second ilium 18 is tightened. As second nut 16 is tightened, the second ilium 18 is pulled into the proper position for fixation as shown in FIG. 10j.

Figure 10K:
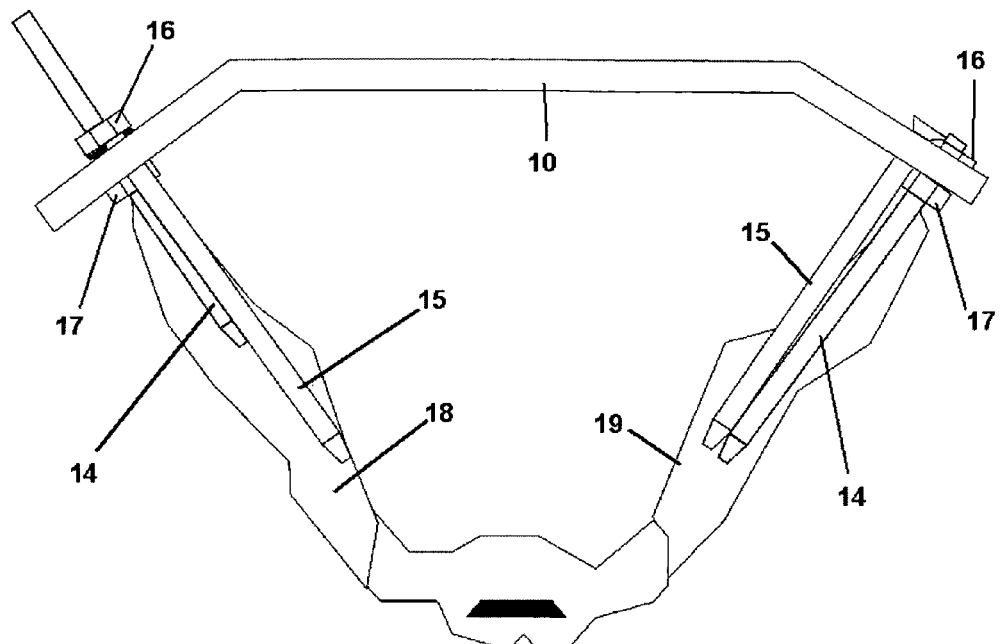
Figure 10L:
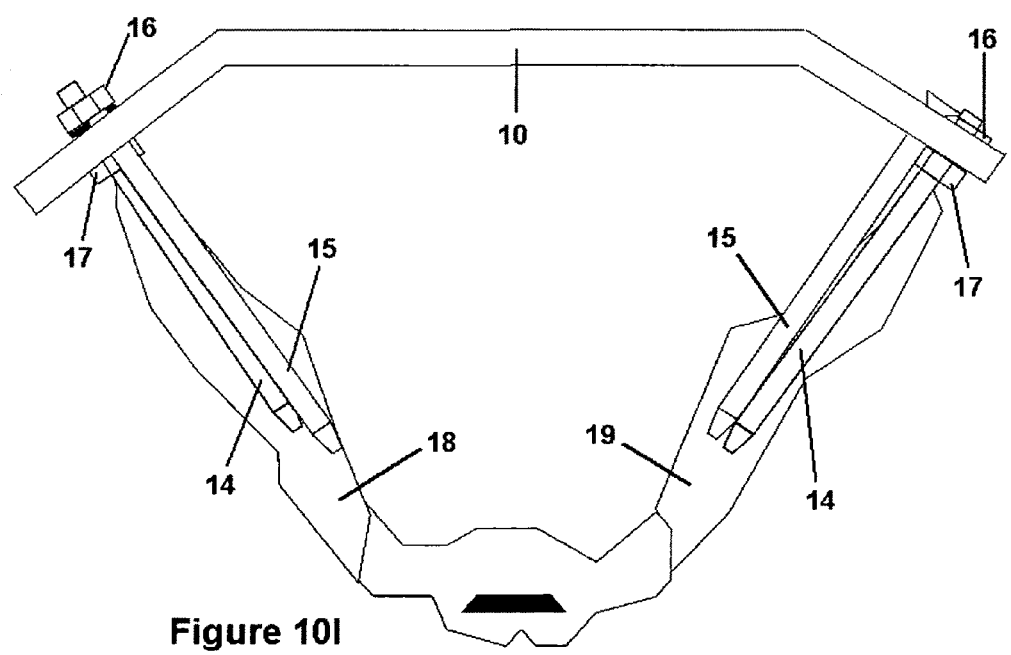

Once the second ilium is pulled into place and second nut 16 is fully tightened, another stabilization screw 15 is inserted into the second ilium 18 through the additional hole 12 in the end of the elongated plate 10 which is adjacent the second ilium 18 as shown in FIG. 10k. Finally, the threaded-rod 14 which is affixed to the second ilium 18 is inserted the rest of the way into the second ilium 18 as shown in FIG. 10l.

This construct and procedure may be used alone (i.e. without posterior fixation) for transporting the trauma patient or with posterior fixation (using, for example, the iliosacral screw technique described above) for a definitive fixation solution. This plate embodiment the capability to help reduce the pelvis when applied.

It is to be expected that considerable variations may be made in the embodiments disclosed herein without departing from the spirit and scope of this invention. Accordingly, the significant improvements offered by this invention are to be limited only by the scope of the following claims.

I claim:

1. A surgical method for minimally invasive treatment of unstable pelvic ring injuries comprising the steps of:
    affixing at least one fixation means to each of the first and second ilium of the pelvis;
    subcutaneously tunneling a single, rigid, anteriorly bowed, elongated plate from one of said fixation means on one ilium to another of said fixation means on the other ilium;

attaching the first end of said elongated plate to at least one of said fixation means on said first ilium; and attaching the second end of said elongated plate to at least one of said fixation means on said second ilium.

2. The surgical method of claim 1, wherein said step of affixing at least one fixation means comprises affixing said fixation means to the supra-acetabular area of each of said first and second ilium of the pelvis.

3. The surgical method of claim 2, wherein said fixation means comprises a threaded rod.

4. The surgical method of claim 3, wherein said step of affixing said threaded rod comprises the steps of:
creating a longitudinal incision centered between the Anterior Inferior Iliac Spine (AIIS) and the Anterior Superior Iliac Spine (ASIS);
bluntly dissecting through the soft tissues;
using fluoroscopic imaging to identify the supra-acetabular starting point for the threaded rod;
opening the cortex of the ilium at said starting point with a drill;
establishing a corridor between the inner and outer cortices of the ilium using a pedicle finder; and
screwing said threaded rod into said corridor.

5. The surgical method of claim 4, wherein said step of screwing said threaded rod into said corridor comprises screwing said threaded rods such that the threaded rod in the second ilium is not initially fully inserted into the second ilium.

6. The surgical method of claim 1, wherein said elongated plate has at least one hole/slot in each end to accommodate said fixation means which affix said plate to said first and second ilium of said pelvis.

7. The surgical method of claim 6, wherein said attaching step further includes the steps of:
threading a first threaded nut onto said threaded rod affixed to said first ilium;
inserting said threaded rod affixed to said first ilium into said hole/slot in one end of said elongated plate, said elongated plate resting on said first threaded nut;
threading a second threaded nut onto said threaded rod affixed to said first ilium; and
tightening said second threaded nut against said elongated plate such that said first threaded nut and said second threaded nut hold said elongated plate securely to said threaded rod affixed to said first ilium.

8. The surgical method of claim 7, wherein said elongated plate further includes a further hole in each end thereof and said method further includes the step of inserting a stabilization screw through said further hole on the end of said elongated plate adjacent to said first ilium and into said first ilium.

9. The surgical method of claim 8, wherein said hole/slot in the end of said elongated plate adjacent to said second ilium is not enclosed by the outer edge of said elongated plate.

10. The surgical method of claim 9, wherein said attaching step further includes the steps of:
threading a first threaded nut onto said threaded rod affixed to said second ilium;
inserting said threaded rod affixed to said second ilium into the hole/slot in the end of said elongated plate adjacent said unstable ilium by slipping the rod through the non-enclosed end of said hole/slot, said elongated plate resting on said first threaded nut;
threading a second threaded nut onto said threaded rod affixed to said second ilium; and
tightening said second threaded nut against said elongate plate such that the second ilium is pulled into the proper position for fixation; and
fully tightening said second threaded nut against said elongated plate such that said first threaded nut and said second threaded nut hold said elongated plate securely to said threaded rod affixed to said second ilium.

11. The surgical method of claim 10, wherein said method further includes the step of inserting a stabilization screw through said further hole on the end of said elongated plate adjacent to said second ilium and into said second ilium.

12. The surgical method of claim 11, wherein said method further includes the step of inserting the threaded rod which is affixed to said second ilium the rest of the way into said second ilium.

13. The surgical method of claim 1, wherein said elongated plate has bends to give the plate an approximation of an arc shape.

14. The surgical method of claim 13, wherein said elongated plate is positioned with the arc anterior to avoid any potential compressive complications to genitourinary or neurovascular structures prior to said step of attaching.

15. The surgical method of claim 1 comprising the further step of leaving said fixation means and said elongated plate attached to the pelvis for 8 to 12 weeks and thereafter removing said fixation means and said elongated plate.

16. The surgical method of claim 1 comprising the further step of stabilizing the posterior instability prior to said step of affixing said fixation means.

17. The surgical method of claim 16 wherein said step of stabilizing the posterior instability comprises inserting at least one iliosacral screw through the rear of one or both of said first and second ilium and into the sacrum.

18. A surgical method for minimally invasive treatment of unstable pelvic ring injuries comprising the steps of:
providing at least two fixation means and a bowed subcutaneous fixation plate, said bowed subcutaneous fixation plate having a first end and a second end;
affixing a first of said at least two fixation means to a first ilium of the pelvis and a second of said at least two fixation means to the second ilium of said pelvis;
subcutaneously tunneling said subcutaneous fixation plate from one of said at least two fixation means on one ilium to another of said at least two fixation means on the other ilium;
attaching said first end of said bowed subcutaneous fixation plate to said first of said at least two fixation means;
attaching said second end of said bowed subcutaneous fixation plate to said second of said at least two fixation means.

19. The surgical method of claim 16, wherein said fixation means are attached to the supra-acetabular area between the Anterior Inferior Iliac Spine (AIIS) and the Anterior Superior Iliac Spine (ASIS) of each of the ilium of the pelvis; and said bowed subcutaneous fixation plate is tunneled in a subcutaneous arc from said first fixation means to said second fixation means and said bowed subcutaneous fixation plate does not arc inferior to a line between the Anterior Inferior Iliac Spine (AIIS) of each ilium and does not arc superior to a line between the Anterior Superior Iliac Spine (ASIS) of each ilium.

* * * * *